(12) United States Patent
Shah et al.

(10) Patent No.: US 8,058,076 B2
(45) Date of Patent: Nov. 15, 2011

(54) IN-VITRO METHOD FOR TESTING BIOEQUIVALENCE OF IRON-SUCROSE FORMULATION

(75) Inventors: Samir Shah, Ahmedabad (IN); Keyur Patel, Ahmedabad (IN); Sanjay Dash, Ahmedabad (IN); Kuldeep Dilip Karnik, Ahmedabad (IN); Ashish Sehgal, Ahmedabad (IN); Bhavesh Vallabhabhai Patel, Ahmedabad (IN); Jayanta Kumar Mandal, Ahmedabad (IN)

(73) Assignee: Astron Research Limited, Gujarat (IN)

( * ) Notice: Subject to any disclaimer, the term of this patent is extended or adjusted under 35 U.S.C. 154(b) by 20 days.

(21) Appl. No.: 12/748,864

(22) Filed: Mar. 29, 2010

(65) Prior Publication Data

US 2010/0248376 A1 Sep. 30, 2010

(30) Foreign Application Priority Data

Mar. 31, 2009 (IN) .......................... 845/MUM/2009

(51) Int. Cl.
*G01N 33/20* (2006.01)

(52) U.S. Cl. ............... 436/84; 436/73; 436/94; 436/100
(58) Field of Classification Search .................. 436/84, 436/73, 94, 100
See application file for complete search history.

(56) References Cited

U.S. PATENT DOCUMENTS

| | | | |
|---|---|---|---|
| 5,624,668 A * | 4/1997 | Lawrence et al. | 424/78.17 |
| 6,911,342 B2 | 6/2005 | Helenek et al. | |
| 6,960,571 B2 * | 11/2005 | Helenek et al. | 514/53 |
| 7,169,359 B2 * | 1/2007 | Helenek et al. | 422/68.1 |
| 7,754,702 B2 * | 7/2010 | Helenek et al. | 514/54 |

* cited by examiner

*Primary Examiner* — Robert J Hill, Jr.
*Assistant Examiner* — Dwan A Gerido
(74) *Attorney, Agent, or Firm* — Hamre, Schumann, Mueller & Larson, P.C.

(57) ABSTRACT

The present disclosure relates to an in vitro method for measuring the $T_{75}$ of reduction kinetics of iron from $Fe^{+3}$ to $Fe^{+2}$ in an iron-sucrose complex and hence assessing the bioequivalency of iron-sucrose composition. According to the disclosed method, $T_{75}$ of reduction kinetics of iron in an iron-sucrose complex in between 25 to 50 minutes indicates bioequivalent iron-sucrose composition.

14 Claims, 6 Drawing Sheets

IN-VITRO METHOD FOR TESTING BIOEQUIVALENCE OF IRON-SUCROSE FORMULATION

FIELD

This disclosure relates to a process for rapid assessment of bioequivalence of iron in iron-sucrose complex, based upon the conversion of $Fe^{3+}$ to $Fe^{2+}$ by breaking the iron sucrose complex without the addition of reducing agent.

BACKGROUND

Iron-carbohydrate complexes, administered either through oral or parenteral route, are used for the treatment of anemia due to iron deficiency. Iron-sucrose injection is widely used in treatment of the iron deficiency and iron deficiency anemia and patients undergoing chronic Hemodialysis receiving supplemental erythropoietin therapy.

Iron-sucrose injection replenishes body iron stores in patients with iron deficiency. Iron is a mineral that the body needs to produce red blood cells. When the body does not get enough iron, it cannot produce the number of normal red blood cells needed to keep a person in good health. This condition is called iron deficiency (iron shortage) or iron deficiency anemia. Iron is sometimes lost with slow or small amounts of bleeding in the body that a person would not be aware of and which can only be detected by a patient's physician. The physician can determine if iron supplement is necessary for the patient.

Some conditions may increase the need for iron in patients. These include bleeding problems, burns, hemodialysis, intestinal diseases, stomach problems, stomach removal, use of medicines to increase red blood cell count, etc.

Iron supplements are available in the following dosage forms:
Oral: Ferrous fumarate, Ferrous gluconate, Ferrous sulfate, Iron-Polysaccharide
Parenteral: Iron-Dextran, Iron-Sorbitol, Iron-Sucrose, Sodium-Ferric-Gluconate Complex In the current scenario, iron-sucrose complex is used orally or parentrally for the treatment of iron deficiency anemia in patients. When iron-sucrose complex is given orally it will not be absorbed 100% from the GI tract. Hence, the absorbed iron-sucrose complex given orally is not adequate to stock up or maintain iron stores necessary for hematopoiesis during erythropoietin therapy.

To have high availability in the conditions like chronic hemodialysis, iron-sucrose is given through intravenous route. Iron sucrose is taken up by cells of the reticuloendothelial system, which release ionic iron that binds to transferrin, which in turn, transfers it to the bone marrow for erythropoiesis or to ferritin and the iron storage pool in the marrow, spleen and liver.

Thus in the human body, the metabolism of iron involves a series of reactions wherein the valence of the iron changes from $Fe^{3+}$ to $Fe^{2+}$ and vice versa.
Metabolism of Iron Sucrose Iron-sucrose is dissociated into iron and sucrose by the reticuloendothelial system and iron is transferred form the blood to a bone marrow. Ferritin, the iron storage protein binds and sequesters iron into a nontoxic iron that is easily available. The iron binds to plasma transferrin which carries iron through the extracellular fluid for supply to the tissues. The transferrin receptors presented in membrane binds transferrin iron complex which is then internalized in vesicles. Further, iron is released within the cell and transferrin-receptor complex returns to the cell membrane. Transferrin without iron is then released to the plasma. The intracellular iron becomes hemoglobin on circulating red blood cells.

When the amount of available iron exceeds ferritin's iron storage mechanism, an aggregated ferritin called hemosiderin is formed, which is a normal constituent of the monocyte-macrophage system. Hemosiderin is composed of molecules of ferritin, which have lost part of their protein shell and become aggregated. Hemosiderin accounts for about one third of normal iron stores and accumulates as insoluble granules in the cells of the reticuloendothelial system.

Upon administration to a patient, an iron-sucrose complex is removed from the blood stream as a particle by the macrophages of the reticuloendothelial system and metabolized to replenish the body's iron stores of hemosiderin, ferritin and transferrin. The rate of removal from the blood stream is dependent on both the colloidal ferric hydroxide's particle size and composition.

Iron-sucrose complex is composed of colloidal ferric hydroxide particles as core in complex with sucrose.

U.S. Pat. No. 6,911,342 claims in vitro method to control and monitor the batch-to-batch bioequivalence of iron-sucrose complexes, by measuring the colloidal ferric hydroxide's rate of reduction from trivalent iron to divalent iron. In the method, iron-sucrose complex is treated with a reducing agent and $T_{75}$ for reduction kinetics of the complex is measured, wherein the $T_{75}$ of less than 20 minutes indicates an effective bioequivalence of iron in the complex.

It is stated in U.S. Pat. No. 6,911,342 that the colloidal ferric hydroxide complexes are dark red to brown solutions with a strong adsorption band at 450 nm. As the reduction to ferrous hydroxide occurs, the color is discharged, resulting in a decrease in absorbency. This decay (or dissociation) can be easily monitored in a temperature controlled ($37\pm1°$ C.) system.

In U.S. Pat. No. 6,911,342, $T_{75}$ time for the reduction of the iron-carbohydrate complex is used to determine the relative bioequivalence by reducing the complex with an appropriate reducing agent. Preferred reducing agents disclosed in the US patent are reduced flavin mononucleotide, dithionite, thioglycolate, hydroquinone, lactate, citrate, bicarbonate, pyruvate, succinate, fructose, cysteine, sorbitol and ascorbic acid. The reducing agent may be present in an amount sufficient to drive the reduction reaction to completion or at least to substantial completion.

A preferred bioequivalence standard for an iron-sucrose formulation is met if $T_{75}$ reduction time is not more than 20 minutes (preferably 9 to 18 minutes) and its reduction reaction plot of "Log(% Trivalent Iron Concentration)" versus "Time" is linear with a correlation coefficient absolute value of not less than 0.98.

Improvement in the method to control and monitor the batch-to-batch bioequivalence of iron-sucrose complexes is desirable.

SUMMARY

The disclosed method provides an in vitro bioequivalence method for iron-sucrose without addition of reducing agent.

In one embodiment, the disclosed method involves determining the kinetics for the conversion of $Fe^{+3}$ to $Fe^{+2}$ in iron-sucrose complex.

The present disclosure also provides experimental proof for the determination of bioequivalent iron-sucrose complex according to the disclosed method.

In one embodiment, the disclosed method is a method of bioequivalence assessment of iron in iron-sucrose complexes, particularly iron-sucrose formulations for routine Quality control (QC) testing. According to the disclosed method, the method of bioequivalence assessment for iron in iron-sucrose complex does not involve addition of a reducing agent.

The disclosed method also includes a method to identify batches of iron-sucrose complexes having substantially the same bioequivalence. The method includes preparing iron-sucrose complexes, determining the conversion kinetics of each batch of iron-sucrose complex and identifying batches of iron-sucrose complex that meet the reduction kinetics of a standard composition of known bioequivalence.

DETAILED DESCRIPTION

Figure 1:
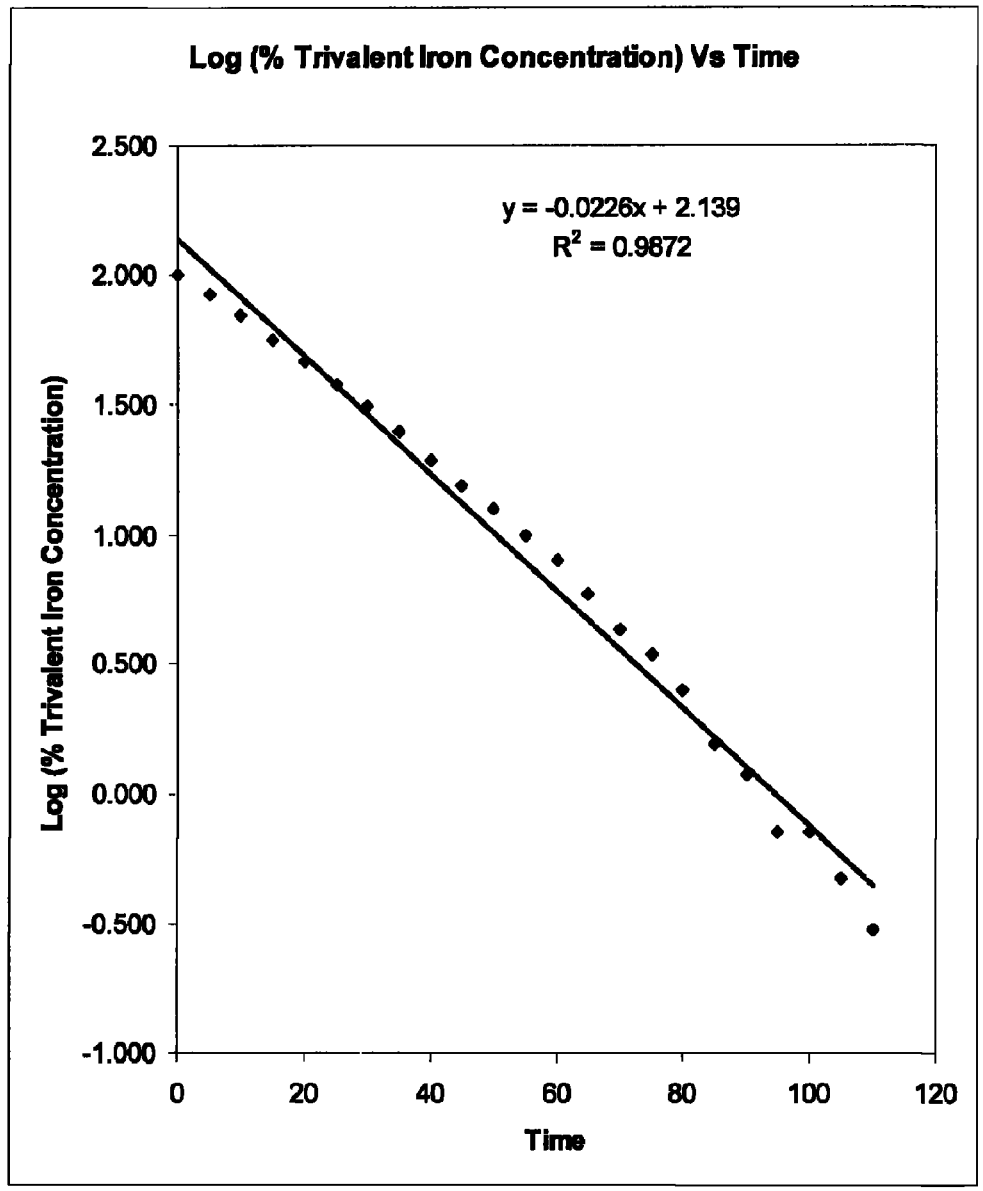
FIG. 1 shows the graph of Log(% Trivalent iron concentration) vs Time for Venofer® used as iron-sucrose injection.

Definition of Terms According to the Present Disclosure

Bioequivalence—Two drugs are said to be equivalent if one drug has the substantially similar plasma concentration profile in the body as compared to another reference drug.

$T_{75}$—Time (in minutes) taken for the dissociation of 75% of iron from iron-sucrose complex.

Reducing agents—A substance capable of bringing about the reduction of another substance as it itself is oxidized. Examples of reducing agents include reduced flavin mononucleotide, dithionite, thioglycolate, hydroquinone, lactate, citrate, bicarbonate, pyruvate, succinate, fructose, cysteine, sorbitol and ascorbic acid.

It has already been established that bioequivalence of iron in iron-carbohydrate complexes may be determined by accessing the kinetics of reduction degradation of iron from $Fe^{+3}$ to $Fe^{+2}$ by using a reducing agent. The disclosed method provides a new, standardized in-vitro method for assessment of bioequivalence of iron in iron-sucrose complex, by measuring $Fe^{+2}$ formed upon the conversion from $Fe^{+3}$, wherein the process is attained without the addition of reducing agent in the presence of an inorganic acid.

Iron-sucrose complex formulations comprises of iron-sucrose complexes which are made up of sucrose complexed with iron (in $Fe^{+3}$ states). According to the disclosed method, in measuring the kinetics of reduction degradation of iron from $Fe^{+3}$ to $Fe^{+2}$ in iron-sucrose complex, a reducing agent is not used in the solution of the disclosed method for measuring the bioequivalence of iron in iron-sucrose complex formulation. The method is carried out in presence of an inorganic acid selected from a group comprising of hydrochloric acid, nitric acid, phosphoric acid and the likes thereof.

In one of the embodiments, kinetics of reduction degradation of iron from $Fe^{+3}$ to $Fe^{+2}$ in iron-sucrose complex is carried out in a solution of hydrochloric acid and without the addition of a reducing agent. The solution used in the said method is 0.25M to 1M hydrochloric acid solution. Preferably, the solution used in the said method is 0.75M hydrochloric acid solution.

pH of the solution used for the in-vitro disclosed method is from about 1.0 to 4.0 pH.

Kinetics of reduction degradation of iron from $Fe^{+3}$ to $Fe^{+2}$ in iron-sucrose complex can be measured using spectrophotometric methods. Conventional spectrophotometric methods include UV/VIS spectroscopy.

Iron-sucrose complexes are dark red to brown solutions with a strong adsorption band at 450 nm. As the reduction of iron from $Fe^{+3}$ to $Fe^{+2}$ occurs, the color is discharged, resulting in a decrease in absorbency. This dissociation can be monitored in a temperature controlled (37±1° C.) UV/VIS spectrophotometer set at 450 nm. Method disclosed in the disclosed method measures the kinetics of reduction degradation of iron from $Fe^{+3}$ to $Fe^{+2}$ without the use of addition of a reducing agent.

According to the disclosed method, it has been found that accessing bioequivalence of iron-sucrose injection can be achieved by measuring $T_{75}$ time for reduction kinetics of iron from $Fe^{+3}$ to $Fe^{+2}$ in a iron-sucrose complex without the addition of reducing agent. It has been found through studies according to the disclosed method that the iron-sucrose solution meets its bioequivalence standard if the $T_{75}$ reduction time of $Fe^{+3}$ to $Fe^{+2}$ in iron-sucrose solution is in between 25 to 50 minutes; preferably $T_{75}$ reduction time of $Fe^{+3}$ to $Fe^{+2}$ in iron-sucrose solution is in between 30 to 40 minutes.

Examples

In-Vitro Assay Method

Sample Preparation:
a) Preparation of 0.75M HCl solution by adding 15.9 ml of concentrated HCl (35%) into 250 ml volumetric flask and make up the volume with purified water.
b) Preparation of Iron-sucrose injection stock solution by adding 1.0 ml of iron-sucrose injection into a 10 ml volumetric flask and make up the volume with purified water Both the above solutions are maintained at 37° C. in a water bath.

c) Method:
Place 2.0 ml of iron-sucrose stock solution into 50 ml volumetric flask, make up the volume with 0.75M HCl solution and mix well.
Take reading on UV/VIS spectrophotometer at 450 nm immediately. Consider the reading as initial.
Continue taking readings on every 5 minutes interval with maintaining 37° C. temperature of sample solution.
Continue taking readings till a constant absorbance is observed.
0.75 M HCl solution is used as blank.

The percentage of iron concentration at a given observation time is calculated by the following equation:

$$100 \times \{(\text{Observed } Abs - \text{Final } Abs)/\text{Initial } Abs - \text{Final } Abs)\}$$

Validation of Method of the Disclosed Method:
The disclosed method for assessing the bioequivalence of iron-sucrose injections can be validated by comparing results obtained for the $T_{75}$ values of commercially available iron-sucrose injection (Venofer®) and sample iron-sucrose sample injections by using the method disclosed in U.S. Pat. No. 6,911,342 and by the disclosed method.

According to U.S. Pat. No. 6,911,342, for an iron-sucrose injection to be bioequivalent with commercially available Venofer®, the $T_{75}$ for the reduction kinetics of the iron-sucrose complex should be less than 20 minutes, preferably 9 to 18 minutes.

The process according to U.S. Pat. No. 6,911,342 is performed as follows:

Sample Preparation:
a) 0.9% Sodium Chloride Preparation
   Prepare diluting solution of 0.9% sodium chloride is prepared (solution A)
b) Stock Solution of Ascorbic Acid Preparation
   Prepare 50 ml stock solution of ascorbic acid (solution B) by dissolving 8.8 grams of ascorbic acid by adding necessary amount of solution A.
c) Stock Solution of Iron-Sucrose Injection Preparation
   Prepare 50 ml stock solution of iron sucrose (solution C) by dissolving 5 ml of iron-sucrose injection solution with purified water Method
   All the above prepared solutions are maintained at 37° C. General procedure involves adding and mixing 20 ml of solution A, 4 ml of solution B and 1 ml of solution C in a flask by maintaining the prepared solution at 37° C. Absorption at 450 nm is measured at predetermined time interval using a UV/VIS spectrophotometer wherein the temperature is constantly maintained at 37° C.

The percentage of iron concentration at a given observation time is calculated by the following equation:

$$100 \times \{(\text{Observed } Abs - \text{Final } Abs)/\text{Initial } Abs - \text{Final } Abs)\}$$

According to the disclosed method, one of the methods for measuring the $T_{75}$ values of reduction kinetics of iron-sucrose complex without using a reducing agent, for accessing the bioequivalence of iron-sucrose injection is performed as follows:

Sample Preparation:
a) 0.75M HCl Preparation
   Added 15.9 ml of concentrated HCl (35%) into 250 ml volumetric flask and make up the volume with purified water.
b) Iron-Sucrose Injection Stock Solution
   Add 1.0 ml of iron-sucrose injection into a 10 ml volumetric flask and make up to volume with purified water.
   Both the above solutions are maintained at 37° C. in a water bath.

Method:
   Place 2.0 ml of iron-sucrose stock solution into 50 ml volumetric flask, make up the volume with 0.75M HCl solution and mix well.
   Take reading on UV/VIS spectrophotometer at 450 nm immediately. Consider the reading as initial.
   Continue taking readings on every 5 minutes interval with maintaining 37° C. temperature of sample solution.
   Continue taking readings till a constant absorbance observed is read.
   0.75 M HCl solution is used as blank.

Studies 1-4 were conducted, where in study 1, commercially available Venofer® was used for the iron-sucrose injection, and in studies 2-4, test samples 1002A, 1004A and 1001A, respectively, were used for the iron-sucrose injection.

The percentage of iron concentration at a given observation time is calculated by the following equation: $100 \times \{(\text{Observed } Abs - \text{Final } Abs)/\text{Initial } Abs - \text{Final } Abs)\}$ Results:
   Results of studies 1-4 obtained where the disclosed method was performed are as shown in the graphs in FIGS. 1-4, respectively. The corresponding values in the graphs depicted in FIGS. 1-4 are shown in Tables 1-4 below, respectively.

TABLE 1

Log(% Trivalent iron concentration) Vs Time for Iron-sucrose injection - commercially available (Venofer ®)

| Time in min. | Abs. at 450 | X = % Trivalent Iron Conc. | Log of X |
|---|---|---|---|
| 0 | 1.747 | 100.0000 | 2.000 |
| 5 | 1.479 | 83.8845 | 1.924 |
| 10 | 1.235 | 69.2123 | 1.840 |
| 15 | 1.013 | 55.8629 | 1.747 |
| 20 | 0.853 | 46.2417 | 1.665 |
| 25 | 0.707 | 37.4624 | 1.574 |
| 30 | 0.603 | 31.2087 | 1.494 |
| 35 | 0.499 | 24.9549 | 1.397 |
| 40 | 0.404 | 19.2423 | 1.284 |
| 45 | 0.341 | 15.4540 | 1.189 |
| 50 | 0.292 | 12.5075 | 1.097 |
| 55 | 0.25 | 9.9820 | 0.999 |
| 60 | 0.216 | 7.9375 | 0.900 |
| 65 | 0.182 | 5.8930 | 0.770 |
| 70 | 0.156 | 4.3295 | 0.636 |
| 75 | 0.141 | 3.4275 | 0.535 |
| 80 | 0.126 | 2.5256 | 0.402 |
| 85 | 0.11 | 1.5634 | 0.194 |
| 90 | 0.104 | 1.2026 | 0.080 |
| 95 | 0.096 | 0.7216 | −0.142 |
| 100 | 0.096 | 0.7216 | −0.142 |
| 105 | 0.092 | 0.4811 | −0.318 |
| 110 | 0.089 | 0.3007 | −0.522 |
| 115 | 0.084 | 0.0000 | #NUM! |

TABLE 2

Log(% Trivalent iron concentration) Vs Time for Iron-sucrose injection - test sample - batch 1002A

| Time in min. | Abs. at 450 | X = % Trivalent Iron Conc. | Log of X |
|---|---|---|---|
| 0 | 1.044 | 100.0000 | 2.000 |
| 5 | 0.88 | 82.6455 | 1.917 |
| 10 | 0.724 | 66.1376 | 1.820 |
| 15 | 0.593 | 52.2751 | 1.718 |
| 20 | 0.494 | 41.7989 | 1.621 |
| 25 | 0.416 | 33.5450 | 1.526 |
| 30 | 0.353 | 26.8783 | 1.429 |
| 35 | 0.307 | 22.0106 | 1.343 |
| 40 | 0.269 | 17.9894 | 1.255 |
| 45 | 0.239 | 14.8148 | 1.171 |
| 50 | 0.211 | 11.8519 | 1.074 |
| 55 | 0.19 | 9.6296 | 0.984 |
| 60 | 0.172 | 7.7249 | 0.888 |
| 65 | 0.157 | 6.1376 | 0.788 |
| 70 | 0.148 | 5.1852 | 0.715 |
| 75 | 0.14 | 4.3386 | 0.637 |
| 80 | 0.132 | 3.4921 | 0.543 |
| 85 | 0.122 | 2.4339 | 0.386 |
| 90 | 0.122 | 2.4339 | 0.386 |
| 95 | 0.116 | 1.7989 | 0.255 |
| 100 | 0.113 | 1.4815 | 0.171 |
| 105 | 0.11 | 1.1640 | 0.066 |
| 110 | 0.105 | 0.6349 | −0.197 |
| 115 | 0.104 | 0.5291 | −0.276 |
| 120 | 0.099 | 0.0000 | #NUM! |

TABLE 3

Log(% Trivalent iron concentration) Vs Time for
Iron-sucrose injection - test sample - batch 1004A

| Time in min. | Abs. at 450 | X = % Trivalent Iron Conc. | Log of X |
|---|---|---|---|
| 0 | 0.973 | 100.0000 | 2.000 |
| 5 | 0.857 | 86.9809 | 1.939 |
| 10 | 0.725 | 72.1661 | 1.858 |
| 15 | 0.594 | 57.4635 | 1.759 |
| 20 | 0.474 | 43.9955 | 1.643 |
| 25 | 0.383 | 33.7823 | 1.529 |
| 30 | 0.325 | 27.2727 | 1.436 |
| 35 | 0.283 | 22.5589 | 1.353 |
| 40 | 0.245 | 18.2941 | 1.262 |
| 45 | 0.213 | 14.7026 | 1.167 |
| 50 | 0.194 | 12.5701 | 1.099 |
| 55 | 0.174 | 10.3255 | 1.014 |
| 60 | 0.154 | 8.0808 | 0.907 |
| 65 | 0.14 | 6.5095 | 0.814 |
| 70 | 0.129 | 5.2750 | 0.722 |
| 75 | 0.121 | 4.3771 | 0.641 |
| 80 | 0.113 | 3.4792 | 0.541 |
| 85 | 0.107 | 2.8058 | 0.448 |
| 90 | 0.101 | 2.1324 | 0.329 |
| 95 | 0.097 | 1.6835 | 0.226 |
| 100 | 0.093 | 1.2346 | 0.092 |
| 105 | 0.092 | 1.1223 | 0.050 |
| 110 | 0.09 | 0.8979 | −0.047 |
| 115 | 0.085 | 0.3367 | −0.473 |
| 120 | 0.082 | 0.0000 | #NUM! |

TABLE 4

Log(% Trivalent iron concentration) Vs Time for
Iron-sucrose injection - sample batch - 1001A

| Time in min. | Abs. at 450 | X = % Trivalent Iron Conc. | Log of X |
|---|---|---|---|
| 0 | 1.699 | 100.0000 | 2.000 |
| 5 | 1.509 | 87.8205 | 1.944 |
| 10 | 1.299 | 74.3590 | 1.871 |
| 15 | 1.123 | 63.0769 | 1.800 |
| 20 | 0.973 | 53.4615 | 1.728 |
| 25 | 0.833 | 44.4872 | 1.648 |
| 30 | 0.731 | 37.9487 | 1.579 |
| 35 | 0.624 | 31.0897 | 1.493 |
| 40 | 0.525 | 24.7436 | 1.393 |
| 45 | 0.450 | 19.9359 | 1.300 |
| 50 | 0.390 | 16.0897 | 1.207 |
| 55 | 0.339 | 12.8205 | 1.108 |
| 60 | 0.299 | 10.2564 | 1.011 |
| 65 | 0.267 | 8.2051 | 0.914 |
| 70 | 0.241 | 6.5385 | 0.815 |
| 75 | 0.216 | 4.9359 | 0.693 |
| 80 | 0.205 | 4.2308 | 0.626 |
| 85 | 0.185 | 2.9487 | 0.470 |
| 90 | 0.173 | 2.1795 | 0.338 |
| 95 | 0.165 | 1.6667 | 0.222 |
| 100 | 0.155 | 1.0256 | 0.011 |
| 105 | 0.152 | 0.8333 | −0.079 |
| 110 | 0.147 | 0.5128 | −0.290 |
| 115 | 0.139 | 0.0000 | #NUM! |

The regression output for graphs in the FIGS. 1-4 are provided in Tables 1a-4a below, respectively.

TABLE 1a

Regression output for FIG. 1

| | |
|---|---|
| Correlation coefficient | (0.994) |
| Constant (b) | 2.139 |
| R Squared | 0.9872 |
| No. of observation | 23 |

TABLE 1a-continued

Regression output for FIG. 1

| | |
|---|---|
| X Coefficient (m) | −0.0226 |
| $T_{75}$ | (1.3979 − b)/m = 32.79 |

TABLE 2a

Figure 2:
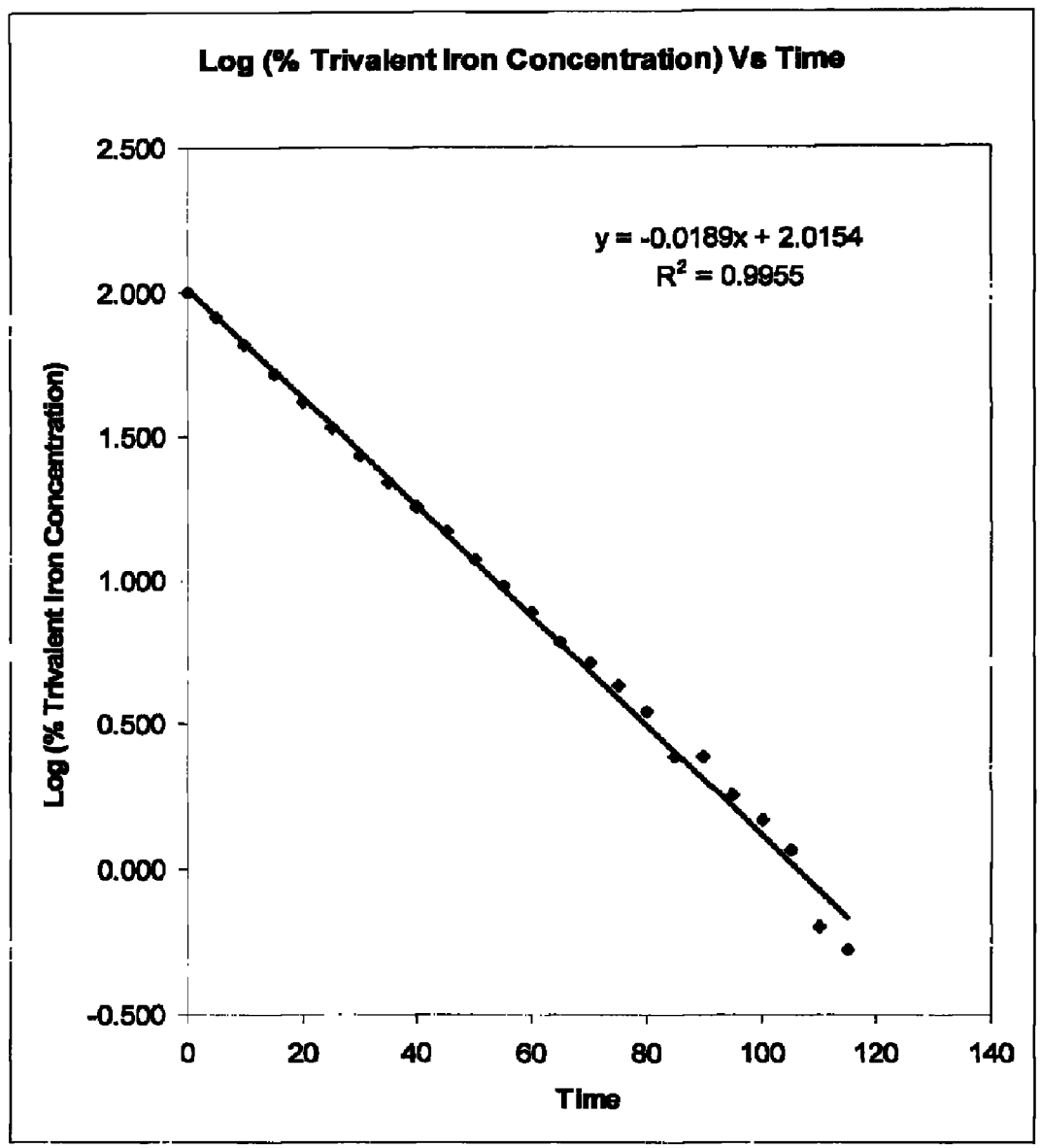
FIG. 2 shows the graph of Log(% Trivalent iron concentration) vs Time for test sample—batch 1002A used as iron-sucrose injection.

Regression output for FIG. 2

| | |
|---|---|
| Correlation coefficient | (0.998) |
| Constant (b) | 2.0154 |
| R Squared | 0.9955 |
| No. of observation | 24 |
| X Coefficient (m) | −0.0189 |
| $T_{75}$ | (1.3979 − b)/m = 32.67 |

TABLE 3a

Figure 3:
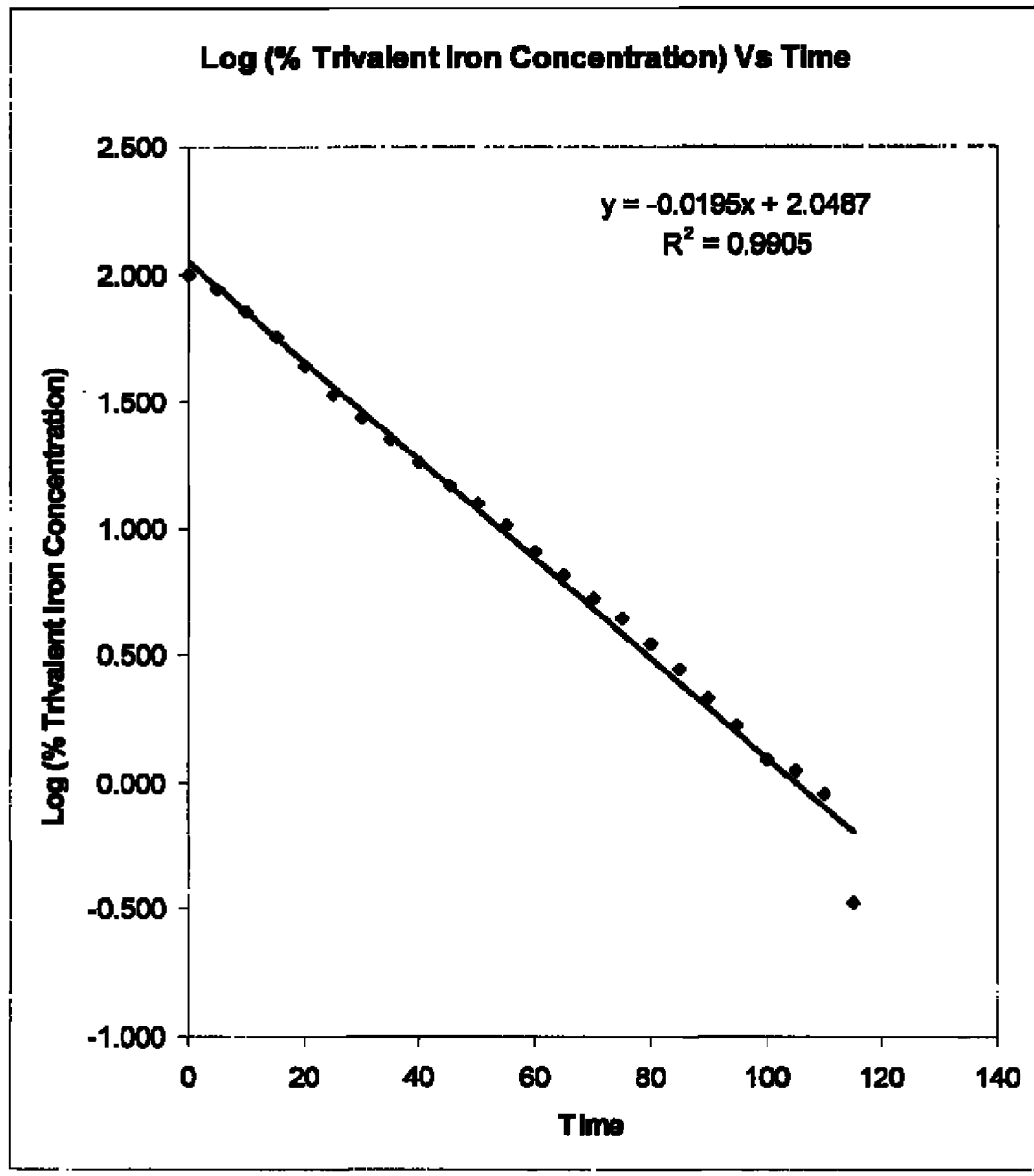
FIG. 3 shows the graph of Log(% Trivalent iron concentration) vs Time for test sample—batch 1004A used as iron-sucrose injection.

Regression output for FIG. 3

| | |
|---|---|
| Correlation coefficient | (0.995) |
| Constant (b) | 2.0487 |
| R Squared | 0.9905 |
| No. of observation | 24 |
| X Coefficient (m) | −0.0195 |
| $T_{75}$ | (1.3979 − b)/m = 33.37 |

TABLE 4a

Figure 4:
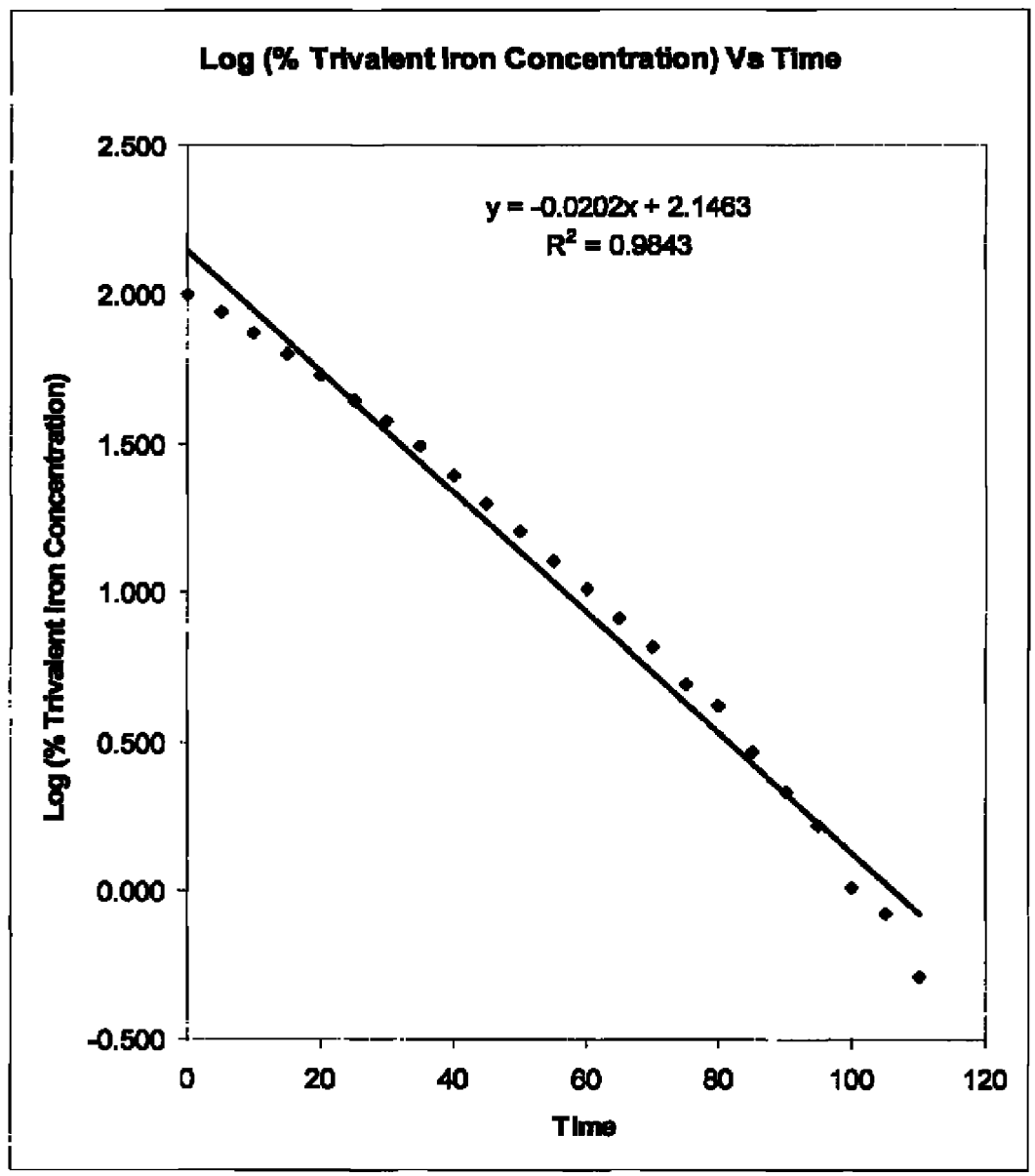
FIG. 4 shows the graph of Log(% Trivalent iron concentration) vs Time for test sample—batch 1001A used as iron-sucrose injection.

Regression output for FIG. 4
Regression output:

| | |
|---|---|
| Correlation coefficient | (0.992) |
| Constant (b) | 2.1463 |
| R Squared | 0.9843 |
| No. of observation | 23 |
| X Coefficient (m) | −0.0202 |
| $T_{75}$ | (1.3979 − b)/m = 37.05 |

Figure 5:
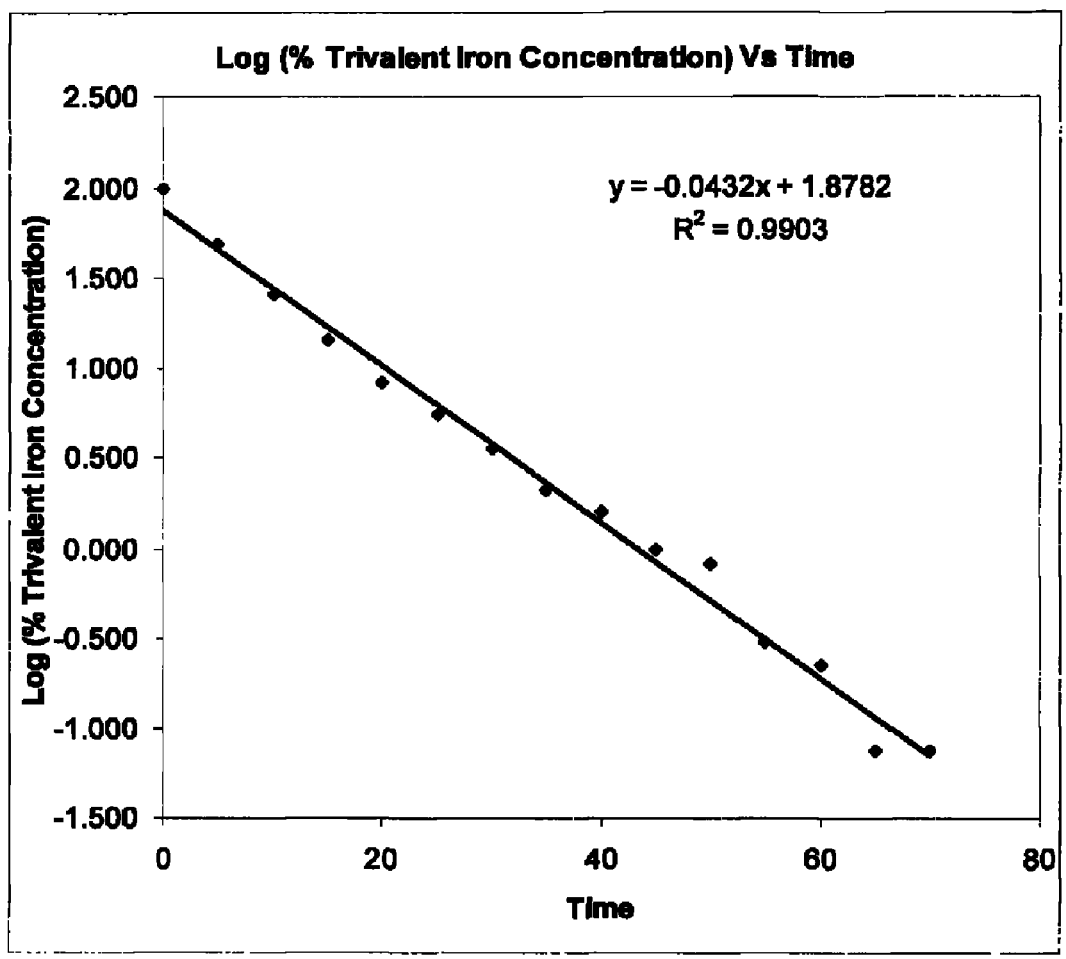
FIG. 5 shows the graph of Log(% Trivalent iron concentration) vs Time for Venofer® used as iron-sucrose injection, according to the process disclosed in U.S. Pat. No. 6,911,342.
Figure 6:
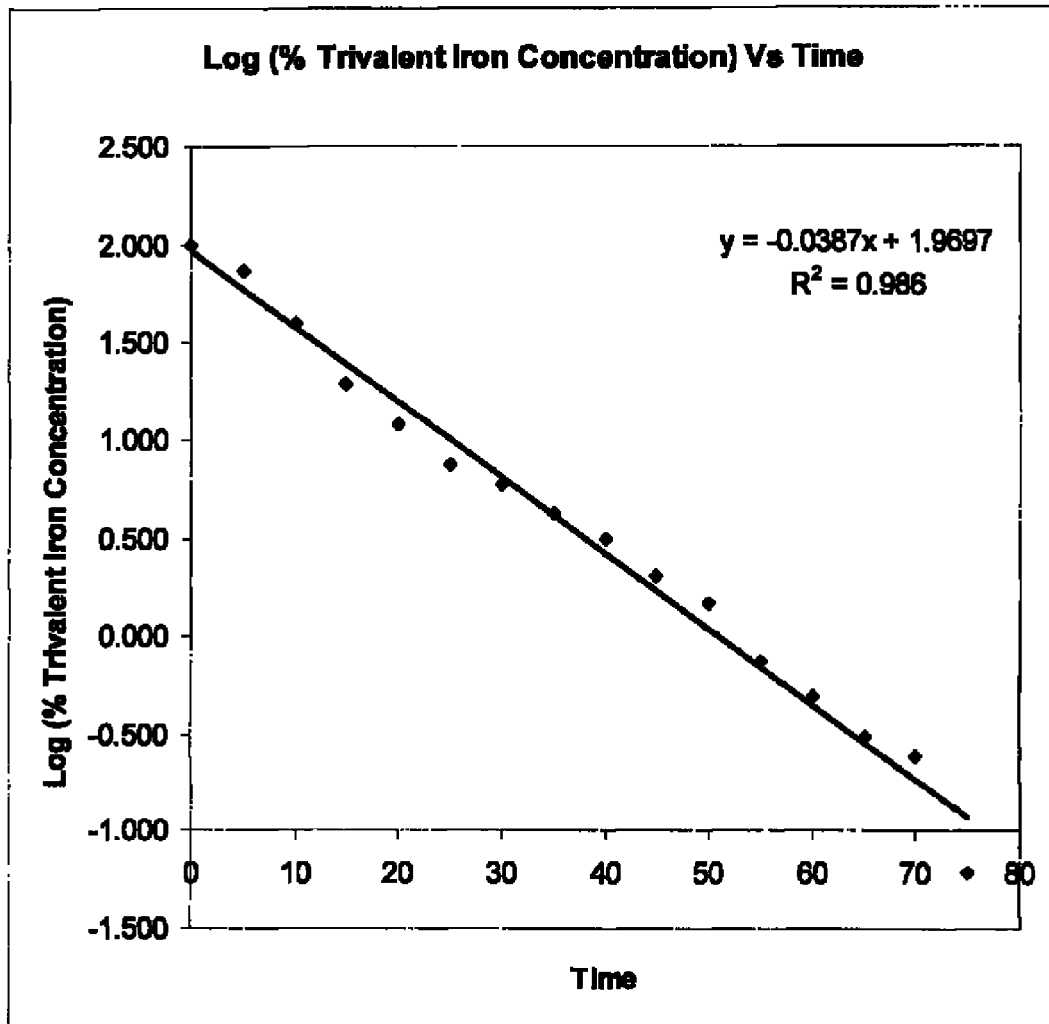
FIG. 6 shows the graph of Log(% Trivalent iron concentration) vs Time for test sample—batch 1001A used as iron-sucrose injection, according to the process disclosed in U.S. Pat. No. 6,911,342.

Results obtained where the method performed as disclosed in U.S. Pat. No. 6,911,342 are shown in FIGS. 5 and 6. The corresponding values for the graphs depicted in FIGS. 5 and 6 are shown in Tables 5 and 6 below.

TABLE 5

Log(% Trivalent iron concentration) Vs Time for
Iron-sucrose injection - Venofer ® - according
to the process disclosed in U.S. Pat. No. 6,911,342

| Time in min. | Abs. at 450 | X = % Trivalent Iron Conc. | Log of X |
|---|---|---|---|
| 0 | 1.352 | 100.0000 | 2.000 |
| 5 | 0.673 | 48.8705 | 1.689 |
| 10 | 0.367 | 25.8283 | 1.412 |
| 15 | 0.213 | 14.2319 | 1.153 |
| 20 | 0.133 | 8.2078 | 0.914 |
| 25 | 0.096 | 5.4217 | 0.734 |
| 30 | 0.071 | 3.5392 | 0.549 |
| 35 | 0.052 | 2.1084 | 0.324 |
| 40 | 0.045 | 1.5813 | 0.199 |
| 45 | 0.037 | 0.9789 | −0.009 |
| 50 | 0.035 | 0.8283 | −0.082 |
| 55 | 0.028 | 0.3012 | −0.521 |
| 60 | 0.027 | 0.2259 | −0.646 |
| 65 | 0.025 | 0.0753 | −1.123 |
| 70 | 0.025 | 0.0753 | −1.123 |
| 75 | 0.023 | −0.0753 | #NUM! |
| 80 | 0.024 | 0.0000 | #NUM! |

TABLE 6

Log(% Trivalent iron concentration) Vs Time for
Iron-sucrose injection - test sample - batch 1001A
according to the process disclosed in U.S. Pat. No. 6,911,342

| Time in min. | Abs. at 450 | X = % Trivalent Iron Conc. | Log of X |
|---|---|---|---|
| 0 | 1.665 | 100.0000 | 2.000 |
| 5 | 1.235 | 73.5385 | 1.867 |
| 10 | 0.691 | 40.0615 | 1.603 |
| 15 | 0.353 | 19.2615 | 1.285 |
| 20 | 0.235 | 12.0000 | 1.079 |
| 25 | 0.161 | 7.4462 | 0.872 |
| 30 | 0.137 | 5.9692 | 0.776 |
| 35 | 0.109 | 4.2462 | 0.628 |
| 40 | 0.091 | 3.1385 | 0.497 |
| 45 | 0.073 | 2.0308 | 0.308 |
| 50 | 0.064 | 1.4769 | 0.169 |
| 55 | 0.052 | 0.7385 | −0.132 |
| 60 | 0.048 | 0.4923 | −0.308 |
| 65 | 0.045 | 0.3077 | −0.512 |
| 70 | 0.044 | 0.2462 | −0.609 |
| 75 | 0.041 | 0.0615 | −1.211 |
| 80 | 0.04 | 0.0000 | #NUM! |

The regression output for graphs in the FIGS. 5-6 are provided in Tables 4a-5a below, respectively.

TABLE 5a

Regression output for FIG. 5

| | |
|---|---|
| Correlation coefficient | (0.995) |
| Constant (b) | 1.8782 |
| R Squared | 0.9903 |
| No. of observation | 15 |
| X Coefficient (m) | −0.0432 |
| $T_{75}$ | (1.3979 − b)/m = 11.12 |

TABLE 6a

Regression output for FIG. 6

| | |
|---|---|
| Correlation coefficient | (0.993) |
| Constant (b) | 1.9697 |
| R Squared | 0.986 |
| No. of observation | 17 |
| X Coefficient (m) | −0.0483 |
| $T_{75}$ | (1.3979 − b)/m = 11.84 |

The results for the Kinetics of reduction degradation of iron from Fe+3 to Fe+2 in iron-sucrose complex are as follows:

| Study # | Batch no. | Process | Calculated $T_{75}$ (in minutes) |
|---|---|---|---|
| 1 | Venofer ® | As per the disclosed method | 32.39 |
| 2 | 1002A | | 32.67 |
| 3 | 1004A | | 33.37 |
| 4 | 1001A | | 37.05 |
| 5 | Venofer ® | As disclosed in | 11.12 |
| 6 | 1001A | U.S. Pat. No. 6,911,342 | 11.84 |

According to study 1-4, it was observed that the $T_{75}$ reduction kinetics of iron-sucrose complex in test samples and commercially available Venofer®, measured using the disclosed method are constant and falling within a specified limit.

According to study 5-6, $T_{75}$ reduction kinetics of iron-sucrose complex in test sample (Batch sample 1001A) and commercially available Venofer® were measured according to the U.S. Pat. No. 6,911,342. Iron sucrose test sample (Batch sample 1001A) was bioequivalent to commercially available Venofer® as the $T_{75}$ reduction kinetic of iron-sucrose complex of both samples were equal and was below 20 minutes.

According to study 1 and 4, $T_{75}$ reduction kinetics of iron-sucrose complex for commercially available Venofer® and test sample (Batch sample 1001A) measured according to the disclosed method are similar and constant.

On comparing the results obtained for measuring the $T_{75}$ reduction kinetics of iron-sucrose complex in test samples and commercially available Venofer® using method disclosed in U.S. Pat. No. 6,911,342 and the disclosed method, the results obtained through the disclosed method are complying and comparable with the results obtained according to the method disclosed in U.S. Pat. No. 6,911,342.

U.S. Pat. No. 6,911,342 describes the criteria of bioequivalence wherein the $T_{75}$ of reduction kinetics of iron in iron-sucrose complex is less than 20 minutes, preferably 9 to 18 minutes. According to the study performed as described in the present disclosure, 11.12 minutes and 11.84 minutes are the $T_{75}$ of reduction kinetics of iron in iron-sucrose complex of commercially available Venofer® and sample batch—1001A respectively, measured using method disclosed in U.S. Pat. No. 6,911,342. Similarly, 32.79 minutes and 37.05 minutes are the $T_{75}$ of reduction kinetics of iron in iron-sucrose complex of commercially available Venofer® and sample batch—1001A respectively measured using disclosed method. It is observed from the studies carried out by the inventors that in the method disclosed in U.S. Pat. No. 6,911,342 and in the disclosed method, there is a difference in result which is in a multiple of 3. Preferable limit for bioequivalency of iron-sucrose product according to U.S. Pat. No. 6,911,342 is 9 to 18 minutes. Hence according to the disclosed method, the limit of acceptance for bioequivalency comes in between 25 and 50 minutes (approximately 3 times the preferable limit as disclosed in U.S. Pat. No. 6,911,342); preferably the T75 reduction kinetics of iron in iron-sucrose complex as per the present disclosure is in between 30 to 40 minutes.

The disclosed method has been described by way of example only, and it is to be recognized that modifications thereto falling within the scope and spirit of the appended claims, and which would be obvious to a person skilled in the art based upon the disclosure herein, are also considered to be included within the scope of the present disclosure.

What is claimed is:

1. A method for accessing the bioequivalence of iron in iron-sucrose injectable composition comprising:
   determining $T_{75}$ for the reduction kinetics of the iron-sucrose complex in a solution of an inorganic acid; wherein the $T_{75}$ in between 25 to 50 minutes indicates an effective bioequivalence of iron in the iron-sucrose complex when administered to a subject.

2. The method as disclosed in claim 1, wherein the solution contains an inorganic acid selected from a group comprising of hydrochloric acid, nitric acid, phosphoric acid and the likes thereof.

3. The method as disclosed in claim 1, wherein the pH of the solution is in between 1 to 4.

4. The method as disclosed in claim 1, wherein the $T_{75}$ is in between 30 to 40 minutes.

5. The method as disclosed in claim 1, wherein the determination of $T_{75}$ for the reduction kinetics is preformed using a spectrophotometric method.

6. The method according to claim 5, wherein the spectrophotometric method comprises of UV/VIS spectroscopy.

7. A method for accessing the bioequivalence of iron in an iron-sucrose injectable composition comprising:
   determining $T_{75}$ for the reduction kinetics of the iron-sucrose complex in a solution without the addition of a reducing agent; wherein the $T_{75}$ in between 25 to 50 minutes indicates an effective bioequivalence of iron in the iron-sucrose complex when administered to a subject.

8. The method as disclosed in claim 7, wherein the solution contains an inorganic acid selected from a group comprising of hydrochloric acid, nitric acid, phosphoric acid and the likes thereof.

9. The method as disclosed in claim 7, wherein the pH of the solution is in between 1 to 4.

10. The method as disclosed in claim 7, wherein the determination of $T_{75}$ for the reduction kinetics is preformed using a spectrophotometric method.

11. The method as disclosed in claim 7, wherein the $T_{75}$ is in between 30 to 40 minutes.

12. A method for accessing the bioequivalence of iron in an iron-sucrose injectable composition comprising:
   determining $T_{75}$ for the reduction kinetics of the iron-sucrose complex in a solution of an inorganic acid and without the addition of a reducing agent; wherein the $T_{75}$ in between 25 to 50 minutes indicates an effective bioequivalence of iron in the iron-sucrose complex when administered to a subject.

13. The method as disclosed in claim 12, wherein pH of the solution is in between 1-4.

14. The method as disclosed in claim 12, wherein the preferable $T_{75}$ is in between 30 to 40 minutes.

* * * * *